United States Patent
Matanguihan et al.

(10) Patent No.: US 6,338,964 B1
(45) Date of Patent: Jan. 15, 2002

(54) PROCESS AND MEDIUM FOR MAMMALIAN CELL CULTURE UNDER LOW DISSOLVED CARBON DIOXIDE CONCENTRATION

(75) Inventors: Ricaredo Matanguihan, Walnut Creek; Eva Sajan, Oakland; Konstantin Konstantinov; Michael Zachariou, both of Walnut Creek; Charles Olson, Moraga, all of CA (US)

(73) Assignee: Bayer Corporation, Berkeley, CA (US)

( * ) Notice: Subject to any disclaimer, the term of this patent is extended or adjusted under 35 U.S.C. 154(b) by 0 days.

(21) Appl. No.: 09/307,175

(22) Filed: May 7, 1999

(51) Int. Cl.$^7$ ............... C12N 5/00; C12N 5/02; C12N 5/06; C12N 5/08
(52) U.S. Cl. .......... 435/404; 435/325; 435/350; 435/352; 435/358; 435/364; 435/366; 435/367; 435/383
(58) Field of Search ................. 435/325, 358, 435/362, 352, 350, 364, 366, 367, 383, 395, 404, 375; 800/362, 352, 350, 364, 366, 367, 375, 383, 395, 404

(56) References Cited

U.S. PATENT DOCUMENTS

| | | | |
|---|---|---|---|
| 4,708,936 A | * 11/1987 | Kulla et al. | 435/128 |
| 5,219,752 A | * 6/1993 | Takazawa et al. | 435/394 |
| 5,527,692 A | * 6/1996 | Hooly et al. | 424/94.64 |
| 5,536,645 A | * 7/1996 | Jay | 435/32 |
| 5,668,108 A | * 9/1997 | Capon et al. | 514/12 |
| 5,831,026 A | * 11/1998 | Almstedt et al. | 530/383 |

FOREIGN PATENT DOCUMENTS

WO    WO-97/38090 A1 * 10/1997

OTHER PUBLICATIONS

Life Technologies Catalog (1994) pp. 1–43, 1–100.*
Yabe et al. (1987) In Vitro Cell Dev. Biol. 23:805–820.*

* cited by examiner

Primary Examiner—Robert A. Schwartzman
Assistant Examiner—Katharine F Davis
(74) Attorney, Agent, or Firm—Melissa A. Shaw; John W. Mahoney

(57) ABSTRACT

A cell culture medium which is low in dissolved carbon dioxide is disclosed. The medium contains less than about 1 g/L added sodium bicarbonate and includes an organic buffer and a metal complexing agent. The medium is preferably essentially free of added sodium bicarbonate. Methods of use of the medium in culturing mammalian cells, particularly cells engineered to produce recombinant factor VIII, are also disclosed.

14 Claims, 9 Drawing Sheets

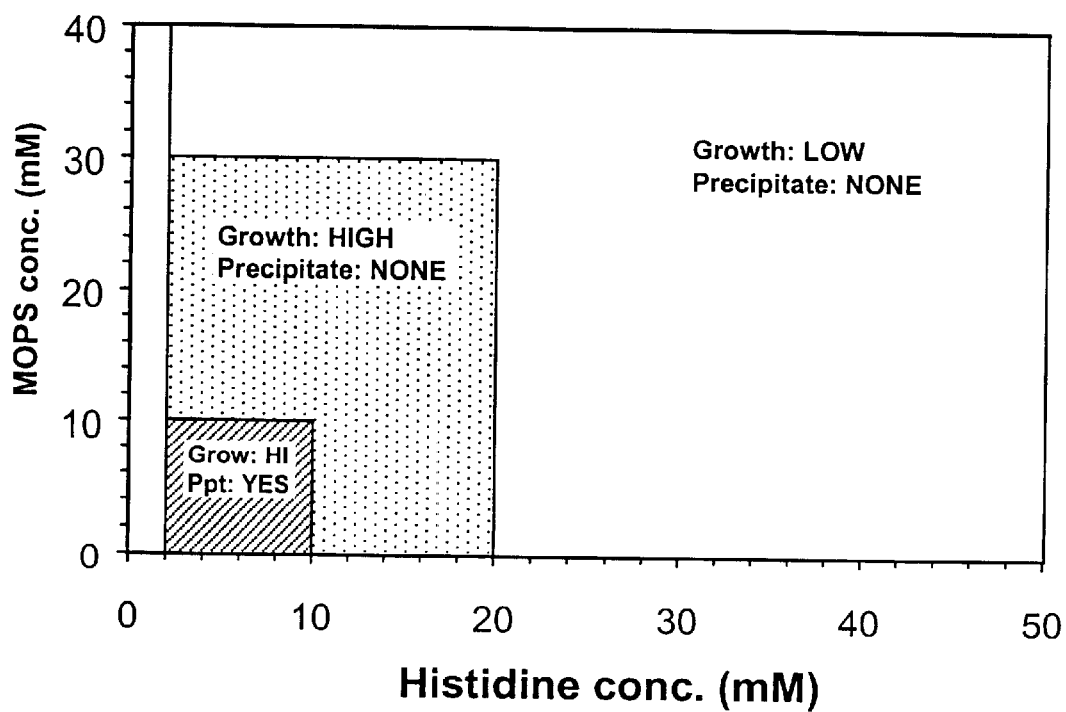
Fig._1

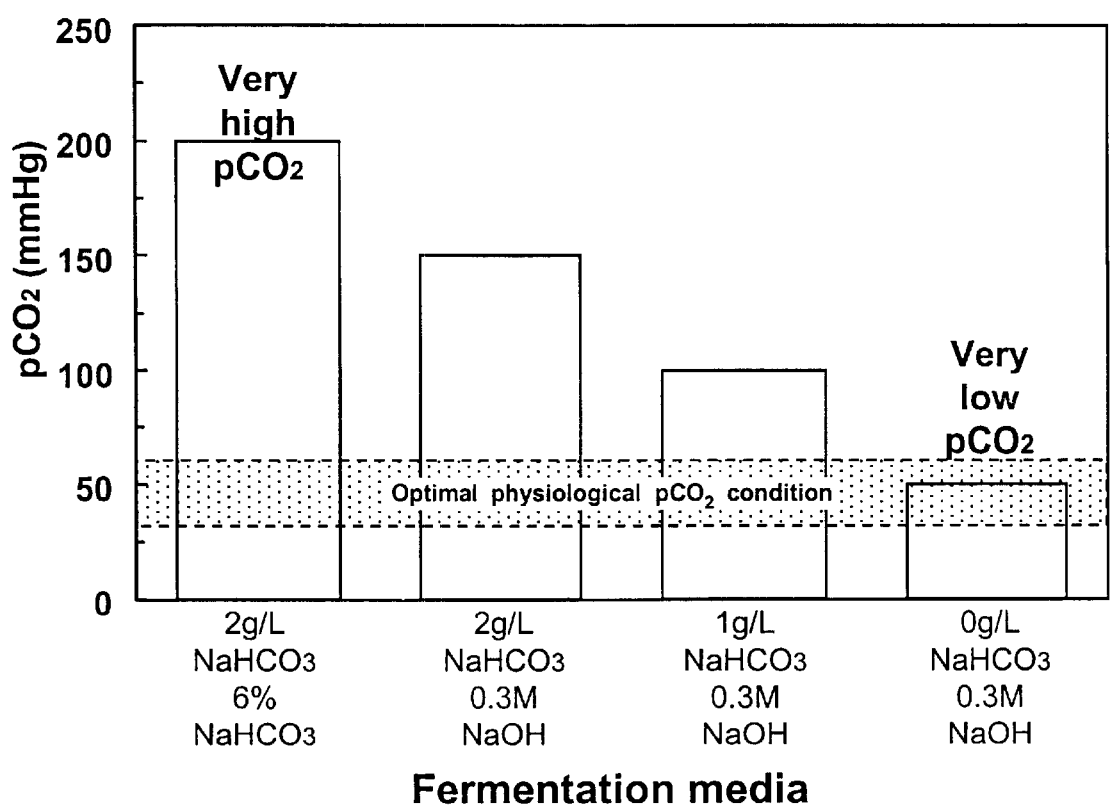
Fig._2

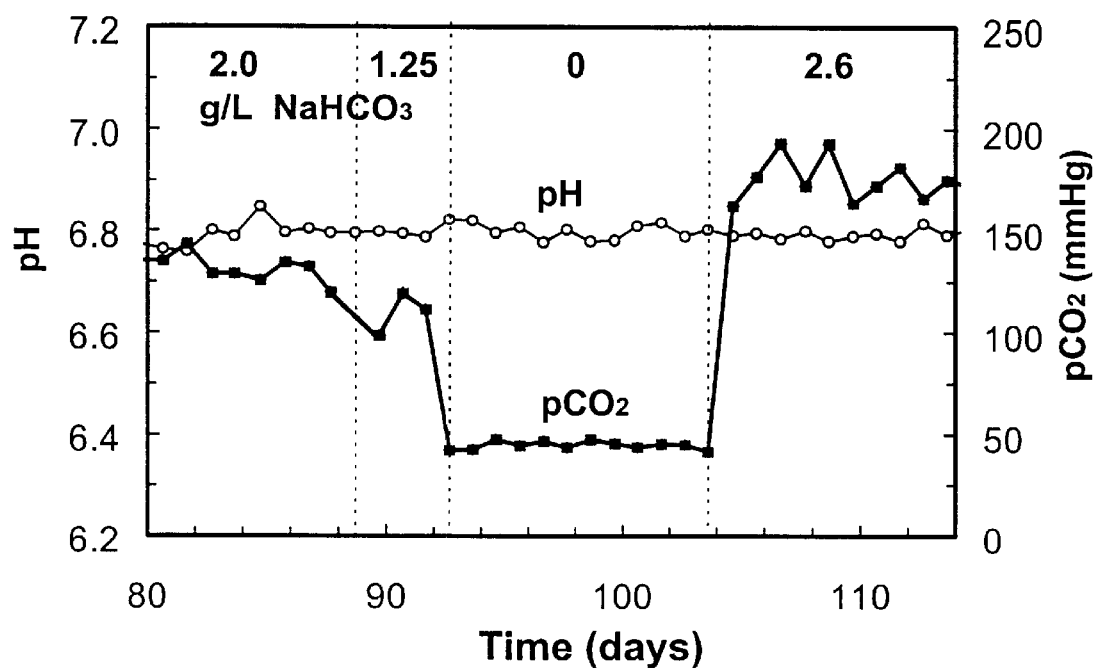
Fig._3

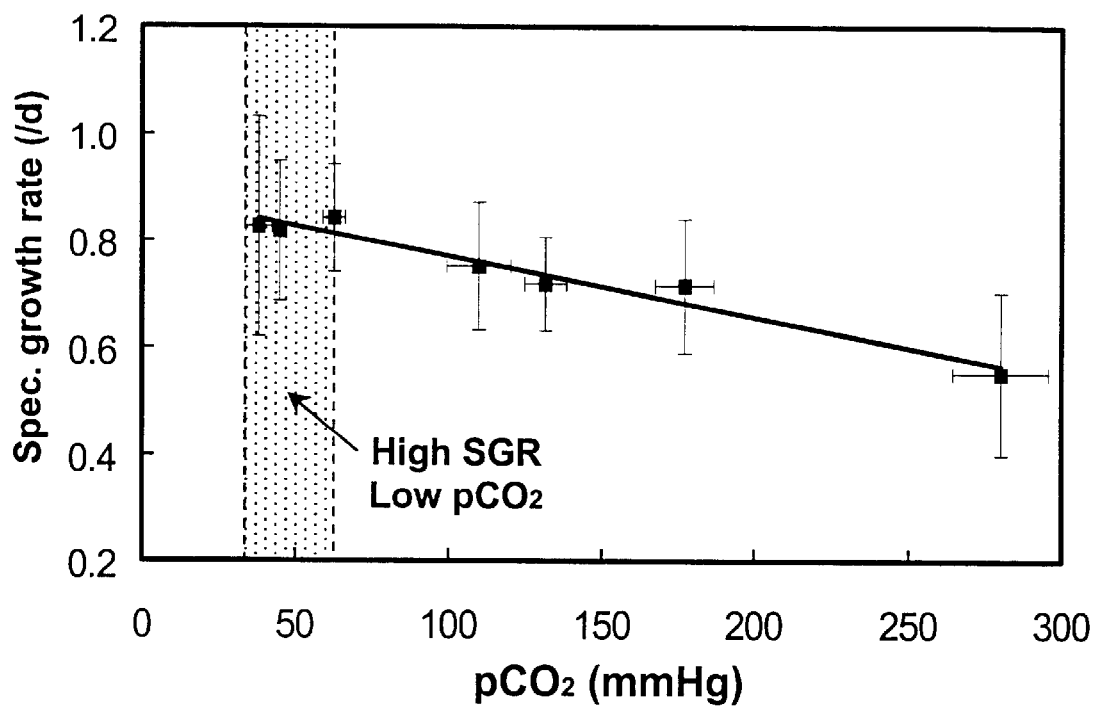
Fig._4

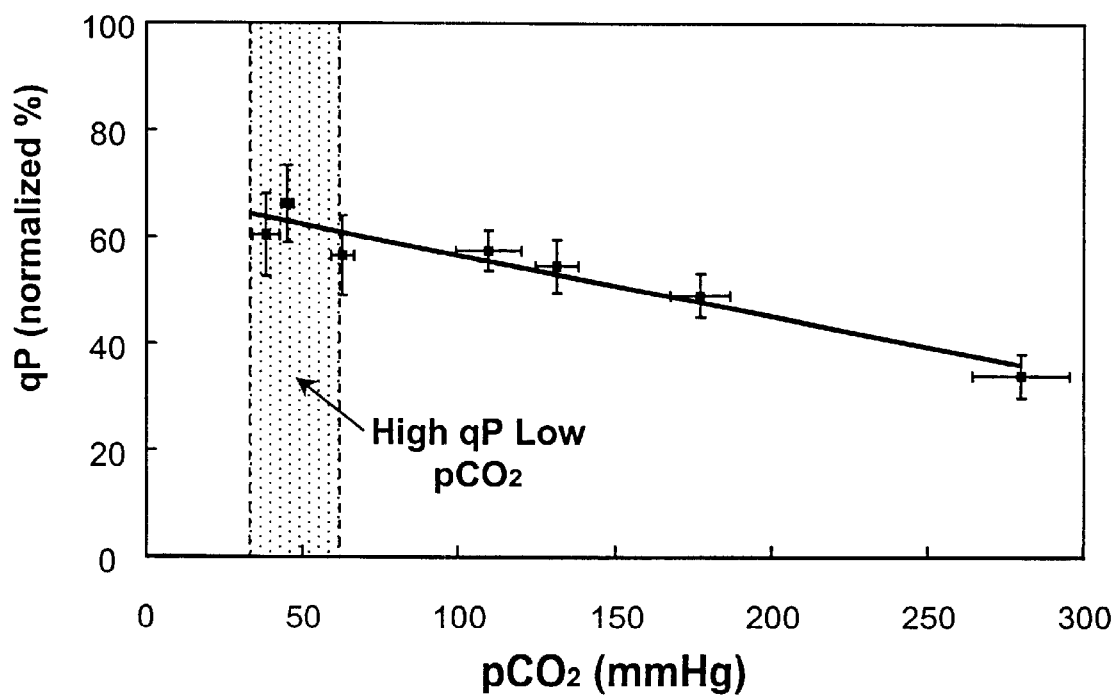
Fig._5

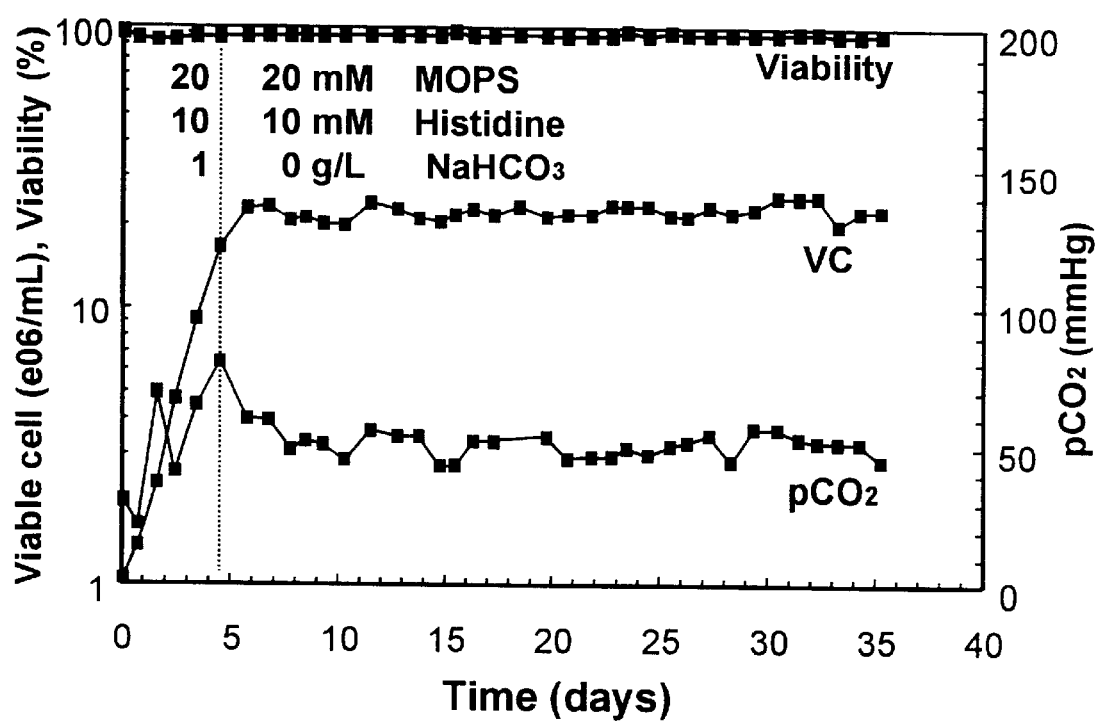
Fig._6

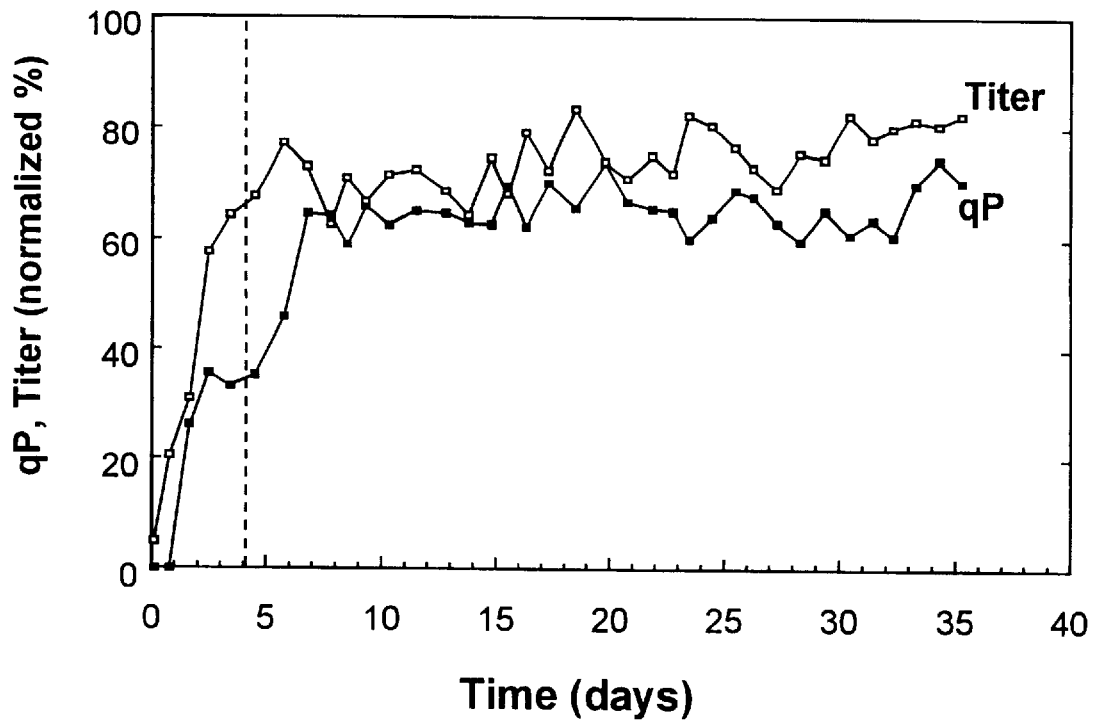
Fig._7

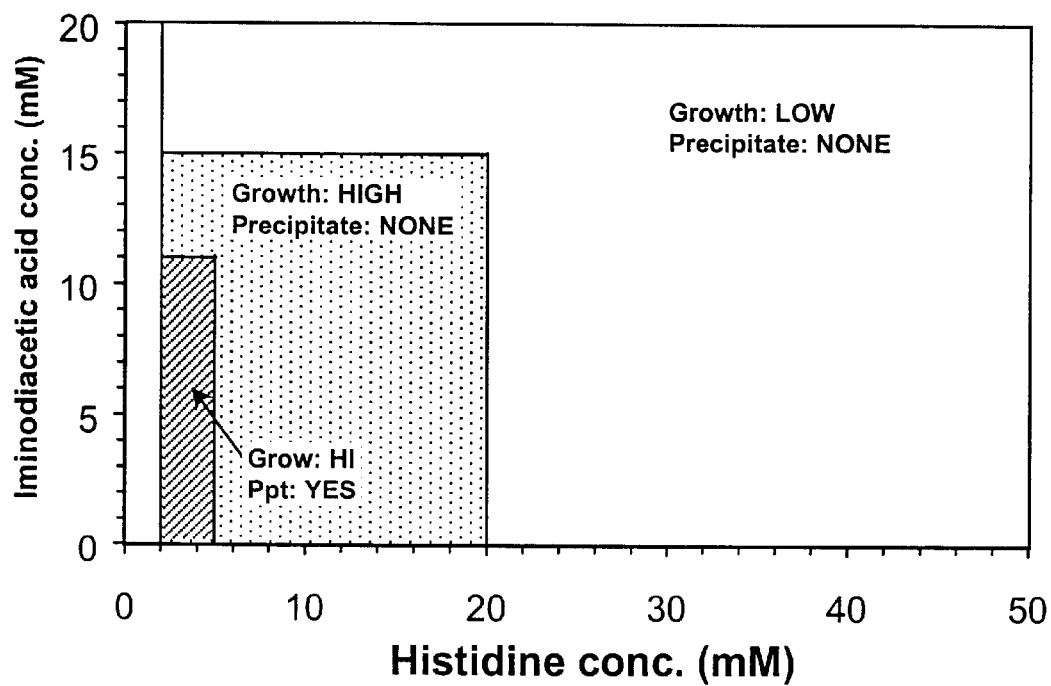
Fig._8

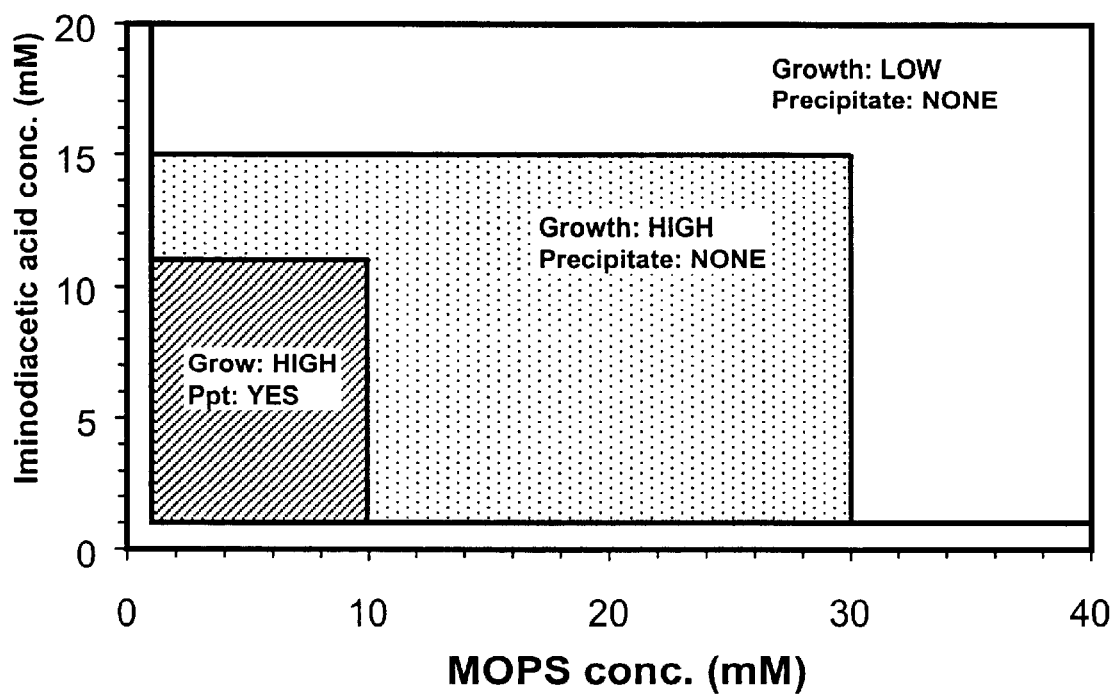
Fig._9

PROCESS AND MEDIUM FOR MAMMALIAN CELL CULTURE UNDER LOW DISSOLVED CARBON DIOXIDE CONCENTRATION

BACKGROUND OF THE INVENTION

1. Field

This disclosure is concerned generally with fermentation and specifically with the control of dissolved carbon dioxide concentration in mammalian cell fermentation, including factor VIII fermentation, using a culture medium containing complexing agents or mixture thereof with organic buffer.

2. Background

Despite the significant physiological role of dissolved carbon dioxide ($DCO_2$) concentration in mammalian and microbial cell fermentation, this parameter has not been monitored, controlled and optimized efficiently. The $DCO_2$ level in the fermentor affects cell intracellular pH (Andersen et al., 1994), which can potentially disturb a number of metabolic pathways. High $DCO_2$ concentration is a major problem because it can inhibit cell growth (Gray et al., 1996; Kimura et al., 1996), can be detrimental to cell metabolism (Gray et al., 1996) and can decrease product formation (Garnier et al., 1996; Gray et al., 1996; Kimura et al., 1996). In mammalian cells, for example, changes in intracellular pH can influence product quality by altering the glycosylation pattern (Andersen et al., 1994; Kimura et al., 1997). For most cell lines, low $DCO_2$ concentration of about 38 mmHg (5%) is adequate for cell growth (Kilburn, 1991). However, typical $DCO_2$ level in high-density mammalian cell perfusion cultures reaches as high as 180–220 mmHg.

The major problem with $DCO_2$ control in fermentation, especially mammalian cell, is the lack of an appropriate method to keep $DCO_2$ concentration low. Common $DCO_2$ control techniques attempt to remove $DCO_2$ by mechanical means, such as by macrosparging. However, macrosparging is not successful at high cell concentrations. Macrosparging also creates foaming problems and can potentially damage the cells. Although there are some techniques to decrease $DCO_2$, these methods are inadequate, difficult to implement, and inappropriate for scale up to manufacturing level. Previously known techniques, including macrosparging in the fermentor and circulating the broth through external membranes, have the above disadvantages.

Sodium bicarbonate ($NaHCO_3$) is the most common and widely used buffer in cell culture media, but it has inherent disadvantages such as generation of very high $DCO_2$ and suboptimal buffering range due to its low pK value of about 6.3 compared typical cell culture pH range of about 6.8~7.4. Some mammalian and microbial fermentation media that are free of $NaHCO_3$ have been reported in the literature. See, e.g., Leibovitz, 1963.

The organic buffer MOPS is present in some cell culture media for cultivating mammalian cells, including hybridoma. See the Table. This buffer has also been used in several media used for growing microbial cells, including fungi and bacteria. A few reported media contain a combination of MOPS as buffer at 5–100 mM and a very low concentration of up to about 0.35 mM histidine. Histidine, an amino acid, is present mainly as nutrient supplement in cell culture media and added at a very low concentration of up to about 1.6 mM. Another culture medium contains a combination of iminodiacetic acid (IDA) and very low histidine nutrient supplement. IDA was previously used as a chelating agent for iron in protein-free media for culturing mammalian cells, including hybridoma cells.

SUMMARY OF THE INVENTION

We have now discovered a method for the control of $DCO_2$ concentration in mammalian and microbial fermentation. This method comprises culturing the cells in a medium which contains a high concentration of a complexing agent and an organic buffer and which is low in added $NaHCO_3$ concentration. Low $NaHCO_3$ concentration is between 0.01 to 1 g/L.

In a more preferred embodiment the medium contains a high concentration of a complexing agent and an organic buffer and is essentially free of added $NaHCO_3$. Essentially free of added

TABLE

Concentration range of complexing agents and organic buffer in culture media.

| Culture medium component (MW) | Application | Reference |
|---|---|---|
| Histidine (155) | | |
| 0.016–0.3 mM (2.5–50 mg/L) | microbial | (Jay, 1996) |
| 1.2 mM (187.5 mg/L) | mammalian | (Wan et al., 1997) |
| 0.35 mM (KG3 medium) | | |
| 1.6 mM | mammalian | (Leibovitz, 1963) |
| MOPS (209) | | |
| 5–50 mM | mammalian, hybridoma | (Dojin Chem Res Inst, 1995) |
| —–30 mM | mammalian, hybridoma | (Nagira et al., 1995) |
| | mammalian | (Cell-Enterprises, 1991) |
| 9.6–95.7 mM (2–20 g/L) | microbial | (Jay, 1996) |
| 9.6 mM (2 g/L) | microbial | (Haxell et al., 1992) |
| | microbial | (Bush et al., 1993) |
| 96 mM (20 g/L) | microbial | (Chartrain et al., 1998) |
| 55.5 mM (10–11.6 g/L) | microbial | (Merck-USA, 1990) |
| 100 mM (21 g/L) | microbial | (Zhang et al., 1996) |
| 4.8 mM (10 g/L) | microbial | (Nakanishi et al., 1992) |
| | microbial | (Edelstein et al., 1993) |
| IDA (133) | | |
| 10 mM | mammalian, hybridoma | (Yabe et al., 1987) |
| 0.130 mM | mammalian | (Bertheussen, 1993) |
| | mammalian | (Ajinomoto, 1991) |
| Complexing agent + Organic buffer | | |
| His (2–50 mM) | mammalian, microbial | NONE |
| His (2–50 mM) + MOPS (0–40 mM) | mammalian, microbial | NONE |
| His (2–50 mM) + IDA (0.2–20 mM) | mammalian, microbial | NONE |
| IDA (0.2–20 mM) + MOPS (2–40 mM) | mammalian, microbial | NONE |

$NaHCO_3$ means that concentration of added $NaHCO_3$ is less than 0.01 g/L, preferrably 0 g/L. "Added" $NaHCO_3$ means manually added to the medium, as opposed to bicarbonate in the medium as a result of normal cell metabolism. In one preferred embodiment the medium includes 2–40 mM histidine as the complexing agent and 1–40 mM MOPS organic buffer. In another preferred embodiment the medium includes a combination of 1–20 mM iminodiacetic acid complexing agent (in lieu of histidine) and 1–40 mM MOPS organic buffer. In another preferred embodiment the medium includes a combination of 1–20 mM iminodiacetic acid complexing agent and 2–50 mM histidine which acts as the buffer while retaining its complexing property. Both IDA and histidine can have complexing and buffering roles. When both are present in the medium, IDA can act as the primary complexing agent since it is a stronger chelating agent than histidine while histidine can act as the buffer since its pK value of about 6.0 is higher and closer to neutral pH compared with IDA.

Generally, complexing agents form a soluble complex with metal ions. Complexing agents may consist of anionic or neutral molecules. A chelating agent is a subgroup of complexing agents characterized by formation of coordination bonds with metal ions in two (bidentate), three (tridentate) or more positions. For example, histidine is a complexing agent because of the single imidazole ring moiety, while IDA (iminodiacetic acid), EDTA (ethylenediaminetetraacetic acid) and citrate are chelating agents through their multiple carboxylic acid functional groups.

A buffer is a system which resists change in pH when a given increment of $H^+$ or $OH^-$ is added. Buffer systems may consist of organic and/or inorganic buffering species such as MOPS, TES, BES (any Goods buffer) or glucose-6-phosphate as examples of organic buffering systems, and $H_2PO_4^-/HPO_4^{2-}$ (phosphate) and $H_2CO_3/HCO_3^-$ (bicarbonate) as examples of inorganic buffering systems.

The fermentation pH using the preferred medium is preferably controlled by automatic and in-line addition of an alkali metal hydroxide solution, e.g. 0.1–0.5 M sodium hydroxide, to the medium line. Using the preferred medium and pH control method, metal ions precipitates are prevented from forming during fermentation. This $DCO_2$ control method significantly decreased the $DCO_2$ concentration in the fermentor and maintained the $DCO_2$ at around physiological level even at high cell concentration for a long cultivation period. The preferred medium maintained high cell growth rate and protein production rate when tested on a variety of cell lines, including, e.g., BHK mammalian cells producing recombinant factor VIII (rFVIII).

It is now possible to solve the $DCO_2$ control and optimization problems in a process using a novel cell culture medium which may optionally be used with the above-described pH control method. Details are described below.

BRIEF DESCRIPTION OF THE FIGURES

FIG. 1 illustrates the concentration range of histidine and MOPS in the culture medium in a preferred embodiment of the invention.

FIG. 2 shows the level of $pCO_2$ in different fermentation media with and without added $NaHCO_3$. The fermentation media (listed on the X-axis) give the concentration of $NaHCO_3$ in the media (top) and the solution used to adjust the pH (bottom) as described herein.

FIG. 3 graphs the pH (squares) and $pCO_2$ (circles) of a continuous perfusion culture where the added medium is altered to include (top of graph) 2.0 g/L, 1.25 g/L, 0 g/L, and 2.6 g/L added $NaHCO_3$.

FIG. 4 charts specific growth rate observed as a function of $pCO_2$. High specific growth rate is one beneficial effect of low $pCO_2$.

FIG. 5 charts specific productivity of rFVIII (normalized to 100%) observed as a function of $pCO_2$. High specific productivity is a significant advantage of low $pCO_2$.

FIG. 6 shows the results observed using the preferred medium containing 10 mM histidine, 20 mM HOPS. Cell viability and viable cell count were maintained at high levels while $pCO_2$ remained low.

FIG. 7 shows the results observed using the preferred medium containing 10 mM histidine, 20 mM HOPS. The medium contained 1 g/L added $NaHCO_3$ during the first four days, which was then omitted during the following 36 days. Specific growth rate and protein production rate (normalized to 100%) were maintained at high and stable levels while $pCO_2$ remained low.

FIG. 8 illustrates the concentration range of iminodiacetic acid and histidine in the culture medium in a preferred embodiment of the invention.

FIG. 9 illustrates the concentration range of iminodiacetic acid and MOPS in the culture medium in a preferred embodiment of the invention.

SPECIFIC EMBODIMENTS

Materials and Methods

This new $DCO_2$ control method was developed and evaluated initially in perfusion culture of mammalian cells, including BHK cell line. The experiment was conducted in a set-up consisting of a stirred-tank fermentor (Applikon Instruments, The Netherlands) with a 15-L capacity equipped with a stirring shaft and impellers in the middle. The fermentor was provided either with a microsparger at the bottom of the vessel or membrane as oxygenation system. The microsparger had a pore size of less than 1000 um, preferably 0.1 to 200 um. The membrane system consisted of silicone tubing wrapped around a metal frame and submerged under the liquid inside the fermentor.

The medium composition was based on commercially available DMEM/F12 formulation manufactured by JRH (Lenexa, Kans.) or Life Technologies (Grand Island, N.Y.) supplied with other essential supplements such as iron, Pluronic F-68, insulin, and essentially free of other proteins (Chan et al., 1998). Complexing agents histidine (his) and iminodiacetic acid (IDA), and organic buffers such as MOPS (3-[N-Morpholino]propanesulfonic acid), TES (N-tris [Hydroxymethyl]methyl-2-aminoethanesulfonic acid), BES (N,N-bis[2-Hydroxyethyl]-2-aminoethanesulfonic acid) and TRIZMA (tris[Hydroxymethyl]aminoethane) were all obtained from Sigma (Sigma, St. Louis, Mo.). The culture medium was supplemented with known concentration of these complexing agents and organic buffers individually or in combination as needed in the experiment. The preferred culture medium also contains EDTA, preferably 50 $\mu$M, as an iron chelating agent. Concentrations in the specification are given as total amount of conjugate acid/base species in solution.

Recombinant BHK cells producing rFVIII were cultivated in the fermentor. Cell cultivation was started by inoculating the 15-L fermentor with cells from previously grown culture in shake-flasks, roller bottles, spinner flasks or another fermentor. Typical essential fermentor parameters were maintained automatically under stable conditions such as temperature at 37° C., pH at 6.8, dissolved oxygen (DO) at 50% of air saturation, stirring speed at 80 rpm, and constant liquid volume. DO and pH were measured on-line using commercially available probes (Mettler-Toledo-Ingold Corp., Wilmington, Mass.). The process started in batch mode for about 1~2 days, and allowed the initial cell concentration to double. This was followed by the perfusion stage wherein the culture medium was pumped continuously into the fermentor and the cell-containing medium was pumped out. A cell separation device was used to separate most of the cells and return them back to the fermentor, while the liquid containing minimal amount of cells, also called harvest, was collected. The medium flow rate was controlled and increased proportionally with the cell concentration. A steady state or stable fermentation process was attained when the cell concentration reached the target high level, preferably 20×10⁶ cells/mL, and was controlled at this concentration. At this point, the medium flow rate also remained constant. As used herein to describe mammalian cell culture systems, "high density" refers to having a cell density of about 5 million to about 50 million cells per milliliter, more preferably about 10 million to about 20 million cells per milliliter, in the culture system.

Fermentor samples were taken at regular time interval, preferably daily, and analyzed off-line by several biological and biochemical methods. Cell concentration was measured using the hemacytometer method and cell viability was determined using the trypan blue dye exclusion technique (Freshney, 1994). The pH, $pCO_2$ (partial pressure of $CO_2$ in mmHg), and $PO_2$ (partial pressure of $O_2$ in mmHg) in the fermentor sample was measured using a Nova analyzer (Model Stat Profile 10, Nova Biomedical, Waltham, Mass.) The corresponding dissolved $CO_2$ ($DCO_2$ in %) in the liquid sample was calculated by dividing $pCO_2$ by 760 mmHg. Similarly, dissolved oxygen (DO in %) in the liquid sample was calculated by dividing the $PO_2$ value by 152 mmHg, the saturation concentration of oxygen in air. Off-line sample values of pH, $pCO_2$ and $PO_2$ were used to verify the pH and dissolved $CO_2$ and $O_2$ level in the fermentor.

EXAMPLE 1

Histidine and MOPS at High Concentration

This $DCO_2$ control method utilized a culture medium comprising a metal complexing agent, e.g. histidine at 2–40 mM, and an organic buffer, e.g. MOPS at 0–40 mM, and essentially free of added $NaHCO_3$ (FIG. 1). Metal complexing agents, like histidine, maintained the solubility of medium components, especially metals. Histidine is a complexing agent at neutral pH because of the imidazole ring moiety. Histidine is also an effective physiological buffer that is suitable at near neutral pH. Similar effects can be achieved by other metal complexing agents such as iminodiacetic acid (see also Yabe et al., 1987; Ajinomoto, 1991; Bertheussen, 1993). MOPS is an effective organic buffer in cell culture, including mammalian cells (Cell-Enterprises, 1991; Dojin Chem Res Inst, 1995). It has a pK value of about 7.0 at 37° C., which is very close to typical fermentation pH. It is also not toxic to cells, including mammalian and microbial, within typical concentration of about 1 to about 100 mM.

Addition of the complexing agent and organic buffer in the culture medium maintained the solubility of medium components, including metal ions, even when 0.3M NaOH was added automatically to the medium line. In the absence of these medium components, precipitates were observed due to a momentary increase in pH after the addition of a strong base such as NaOH. High pH favored the formation of several metal hydroxides such as magnesium hydroxide. The precipitate in the medium line was identified as containing primarily magnesium hydroxide.

EXAMPLE 2

Effective Control of Dissolved $CO_2$

This new method was used and applied successfully to control and minimize the dissolved $CO_2$ concentration in continuous perfusion fermentation of Baby Hamster Kidney (BHK) cells producing recombinant factor VIII (rFVIII). Dissolved $CO_2$ level decreased about five-fold from about 190 mmHg to 40 mmHg partial pressure by switching from the regular medium containing 2 g/L $NaHCO_3$ at pH 6.8 to a medium without any $NaHCO_3$ (FIG. 2). This low $DCO_2$ condition was maintained consistently using the preferred medium, even though the cell concentration reached a high level of at least $20 \times 10^6$ cells/mL (FIG. 3). The pH remained stable and under good control, despite the absence of $NaHCO_3$ in the medium, by automatic addition of 0.3M NaOH solution (FIG. 3).

Even in the case when a $NaHCO_3$-containing medium was used, a significant decrease in $DCO_2$ concentration was realized by using 0.3M NaOH instead of 0.7M $NaHCO_3$ for pH control because it did not add $CO_2$ into the fermentor liquid (FIG. 2). As shown in a long term perfusion fermentation, the $pCO_2$ level decreased by about 50 mmHg from 200 to 150 mmHg, using a 0.3M NaOH for pH control in a medium with 2 g/L $NaHCO_3$ (FIG. 3).

In the case when a medium contains up to 1 g/L $NaHCO_3$, a proportional decrease of about 50% in $pCO_2$ concentration from the initial level of 200 mmHg was realized (FIG. 2). This decrease in $pCO_2$ was similarly significant. This culture medium is also useful and preferred when starting cell cultivation at low mammalian cell concentration of less than $1.0 \times 10^6$ cells/mL, since the $pCO_2$ concentration could be lower than the typical cell physiological level of about 38 mmHg, which is equivalent to 5%. Cell cultivation procedures (Kilburn, 1991) and previous experimental observations or protocols suggested the use of 5% $CO_2$ to promote cell growth at the start of the culture especially at low cell concentration, while it also assists to control pH. This phenomenon demonstrated the peculiar role of $CO_2$ in mammalian cell culture as a major biochemical product of cell respiration and as substrate or growth requirement. The explanation of this phenomenon has not been clearly established.

EXAMPLE 3

Physiological Benefits of Low $DCO_2$

The experiment to study the physiological effect of different $DCO_2$ concentration was conducted in a perfusion cultivation using a 15-L fermentor as described in the Material and Methods section. Cells were rFVIII-producing BHK cell line, while the culture medium contained different $NaHCO_3$ concentrations at different phases. Complexing agents and buffers other than $NaHCO_3$ were not used in this initial experiment. When the cultivation reached the steady-state phase at high cell concentration, the $DCO_2$ level were varied by changing the $NaHCO_3$ content of the medium (FIG. 3). The process were maintained at each $DCO_2$ level for reasonable period of at least five days to ensure accurate and reliable data.

Viable cell concentration remained constant at about $20 \times 10^6$ cells/mL, and cell viability remained very high, i.e. above 90%, at both low (40 mmHg) and moderate (150 mmHg) $DCO_2$ levels. These results were illustrated by the significant and proportional increase in specific growth rate at lower $DCO_2$ concentration, thereby demonstrating one major advantage of controlling $DCO_2$ at low level (FIG. 4). This is a significant finding which can improve mammalian cell culture protocol in general.

The other major beneficial effect of lower $DCO_2$ in fermentation, including rFVIII fermentation, was high specific production rate at low $DCO_2$ condition (FIG. 5). This is an important process advantage of this $DCO_2$ control method because there will be more product at the same fermentor capacity, fermentation time, and culture medium volume. Another experiment obtained similar findings and demonstrated the advantage of low $DCO_2$ in rFVIII fermentation.

On the other hand, very high $DCO_2$ at about 300 mmHg was clearly detrimental to the cell, as shown by the significant decrease in specific growth rate (FIG. 5) and specific production rate (FIG. 6). Such an unfavorable fermentation condition should be avoided during cell culture. In the absence of an effective $DCO_2$ control means, mammalian cell fermentation would not reach very high cell concentration and would not attain high protein production.

Process Consideration of Low $DCO_2$ Control

One observation in this experiment was precipitate formation in the medium line, right after the junction where 0.3M NaOH was added to control pH in the fermentor. Most of the precipitate were flushed in the fermentor, but some precipitate accumulated in the tubing over a very long period of time of at least three days. One disadvantage of precipitate accumulation was mechanical obstruction in liquid flow and resulted to process disturbance. This problem was not practical in long term operation and several means and extensive tests were evaluated to avoid or remedy this precipitate formation. Addition of complexing agent and buffer was the most feasible and reliable technique to prevent precipitation, as described in the following example.

EXAMPLE 4

Culture Medium with Histidine and MOPS

Another experiment using the same BHK cells was set up as described in the Materials and Methods section and in Example 3. In this case, the preferred initial culture medium contained 10 mM histidine, 20 mM MOPS and 1 g/L $NaHCO_3$, and then after five days switched to the more preferred medium containing similar concentration of histidine, MOPS and essentially free of $NaHCO_3$. The same fermentation conditions were maintained throughout the cultivation, similar sample analyses were performed. Results demonstrated consistently high cell concentration and very high cell viability while keeping low $DCO_2$ concentration in the experiment (FIG. 6). In addition, there was no precipitate formation in the medium line in contrast to earlier observations in Example 3, throughout the duration of the experimental run. At the same, similar physiological benefits were realized at low $DCO_2$. Specific growth rate and protein production rate both remained high and stable, indicating favorable cell physiology and metabolism in the most preferred culture medium (FIG. 7).

EXAMPLE 5

Iminodiacetic Acid and Histidine

This experiment using similar BHK cells and set-up described in Materials and Methods section was performed by adding another complexing agent, iminodiacetic acid (IDA), to the culture medium. The preferred culture medium contained a combination of high concentration of iminodiacetic acid (IDA), which acted as the primary complexing agent, and histidine which assumed the buffer function as well as complexing ability. Although both IDA and histidine had complexing properties, IDA was relatively a stronger complexing agent than histidine. At the same time that both could act as buffers, histidine could function as the main buffer since its effective pK value of about 6.0 was closer to near neutral cultivation pH. In this preferred embodiment the medium consisted of 0.2 to 20 mM IDA and 2 to 50 mM histidine (FIG. 8). The more preferable combination was 10 mM IDA and 10 mM histidine. This preferred medium similarly controlled $DCO_2$ at the low level close to physiological pH, maintained high cell growth rate and viability, sustained high FVIII production rate, and prevented precipitate formation in the medium line.

EXAMPLE 6

Iminodiacetic Acid and MOPS

In another experiment using similar BHK cells, fermentor set-up and cultivation conditions described in Materials and Methods section, the preferred culture medium contained a combination of 1–20 mM IDA complexing agent (in lieu of histidine) and 1–40 mM MOPS organic buffer (FIG. 9). The more preferable combination of 10 mM IDA and 20 mM MOPS in the medium similarly maintained low $DCO_2$, high cell growth rate and viability, high rFVIII production rate, and prevented precipitate formation in the medium line.

EXAMPLE 7

Selection of Complexing Agent and Organic Buffer

Histidine and iminodiacetic acid (IDA) were selected as preferred complexing agents after experimental evaluation of several complexing agents such as ortho-phospho-L-serine (OPS), citrate, EDTA, aurintricarboxylic acid (ATA) and lysine hydroxamate. The experiment was conducted by measuring cell growth and viability of BHK cells in small-scale shake flask culture at different complexing agent concentrations for several days. Additional tests were performed in 15-L perfusion fementation, and selection criteria were cell physiology, protein production and precipitate formation.

Very low concentrations (<0.2 mM) of complexing agents, especially the specific subgroup classified as chelating agents, have been included in protein-free cell culture medium. Chelating agents in protein-free culture media enhance the solubility and availability of iron (Fe) in the absence of transferrin. Transferrin is a protein that carries iron into cells and is a common component of protein-containing or serum-supplemented culture media. Examples of chelating agents are EDTA (Medi-cult, 1988; Gilbert et al., 1998) and citrate (Kovar et al., 1987; Medi-cult, 1988; Tung et al., 1988; Novo-Nordisk, 1993; Nagira et al., 1995), tropolone (2-hydroxy-cycloheptatrienone) (White et al., 1976; Celltech, 1994; Gilbert et al., 1998), and ATA (aurintricarboxylic acid) (Medi-cult, 1988). IDA alone was previously used in protein- free cell culture medium as a chelating agent for iron (Ajinomoto, 1991; Bertheussen, 1993). IDA at a higher concentration (10 mM) was also used in hybridoma cell medium (Yabe et al., 1987).

MOPS was selected as a preferred organic buffer after experimental evaluation of several buffers such as imidazole, ADA, ACES, BIS-TRIS, BICINE, BIS-TRIS Propane, BES, GLYGLY, HEPES, MOPS, MOPSO, PIPES, TES, TAPSO, TRIZMA and TRICINE. The experiment was conducted by measuring cell growth and viability of BHK in small-scale shake flask culture at different buffer concentrations for several days. Additional tests were performed using MOPS, BES, TES, TRIZMA, HEPES and PIPES in 15-L perfusion fermentation, and selection criteria were cell physiology, protein production and precipitate formation. When BES, TES, and TRIZMA were each used, precipitate formation did not occur, however less favorable cell growth and production rate as compared to MOPS were observed. Several of these buffers were previously used in cell culture media (Custer et al., 1990; Swim and Parker, 1955; Itagaki et al., 1974).

EXAMPLE 8

Applicability in Other Cell Types

The culture medium described herein can be applied in other mammalian and in other animal cell lines, as well as microbial cells. Most common mammalian cells, such as BHK, CHO (chinese hamster ovary), HEK (human embryonic kidney), HeLa (human cervical carcinoma), L cells (mouse connective tissue), MDCK (Madin Darby canine kidney), and Vero cells (African green monkey kidney) and different lines of hybridomas generally have similar growth trend and nutrient requirements such as sugars, amino acids, vitamins, growth factors, salts, and trace metals in the case of serum-free media (Wolfe, 1993; Freshney, 1994). Experimental results for BHK cells indicated high cell growth based on viable cell count and cell viability in culture medium containing histidine level up to 50 mM, MOPS level as high as 40 mM, and iminodiacetic level reaching 20 mM.

Cultivation conditions which influence and support good cell growth and metabolism typically fall in the following ranges: temperature of about 34–37° C., DO level within about 30–60%, and pH of about 6.8–7.4. The best conditions and combination of these parameters may vary a little depending on the cell line as well as the product. Given the teaching herein, the optimization of these conditions is easily practicable.

CONCLUSION

In general, existing mechanical methods for $DCO_2$ removal relying on enhanced mass transfer are inefficient, and cannot reduce $DCO_2$ down to optimal physiological levels of ~40 mmHg. In contrast to all these methods which attempted to remedy the high $DCO_2$ problem, a new method was developed which avoided the problem up front and completely. This method to control $DCO_2$ concentration in fermentation comprises using a culture medium which contains a metal complexing agent and an organic buffer and which is essentially free of added $NaHCO_3$. Control of pH was carried out by addition of NaOH to the medium feed line. This method does not require additional hardware or accessories other than what is already available in a typical fermentation set-up.

The above examples are intended to illustrate the invention and it is thought variations will occur to those skilled in the art. Accordingly, it is intended that the scope of the invention should be limited only by the claims below.

REFERENCES

Ajinomoto, Jap. Pat. No. J03201981 (1991)

Andersen D C et al., The effect of cell-culture conditions on the oligosaccharide structures of secreted glycoproteins, Curr. Opin. Biotechnol. 5: 546–549 (1994)

Bertheussen K, Growth of cells in a new defined protein-free medium, Cytotechnology. 11: 219–231 (1993)

Bush B D et al., Carbocyclic nucleosides from a species of Saccharothrix, Phytochemistry. 32: 737–739 (1993)

Cell-Enterprises, U.S. Pat. No. 5,045,468 (1991)

Celltech, WIPO Pat. No. 94/02592 (1994)

Chan S-Y et al., U.S. Pat. No. 5804420 (1998)

Chartrain M M et al., WIPO Pat. No. 98/03672 (1998)

Custer L et al., Various zwitterionic buffers support the growth of hybridomas and Chinese hamster ovary cells in culture, In Vitro. 26: 37A (1990)

Dojin-Chem Res Inst et al., Jap. Pat. No. JP07107970 (1995)

Edelstein P H et al., Comparison of three buffers used in the formulation of buffered charcoal yeast extract medium, J. Clin. Microbiol. 3329–3330 (1993)

Freshney R I, Culture of animal cells: A manual of basic technique, John Wiley & Sons, New York, pp. 268–289 (1994)

Garnier A et al., Dissolved carbon dioxide accumulation in a large scale and high density production of TGF-Beta receptor with baculovirus infected Sf-9 cells, Cytotechnology. 22: 53–63 (1996)

Gilbert R S et al., Alternatives to transferrin in serum-free media for recombinant virus and protein production, Cell Culture Engineering VI, San Diego, Calif. (1998)

Gray D R et al., $CO_2$ in large-scale and high-density CHO cell perfusion culture, Cytotechnology. 22: 65–78 (1996)

Haxell M A et al., C-13beta-acyloxymilbemycins, a new family of macrolides—discovery, structural determination and biological properties, J. Antibiot., 45: 659–670 (1992) Itagaki A et al., TES and HEPES buffers in mammalian cell cultures and viral studies:

Problem of carbon dioxide requirement, Expt Cell Res., 83:351–361 (1974).

Jay C, U.S. Pat. No. 5,536,645 (1996)

Kimura R et al., Effects of elevated pCO2 and/or osmolality on the growth and recombinant tPA production of CHO cells, Biotechnol. Bioeng. 52: 152–160 (1996)

Kimura R et al., Glycosylation of CHO-derived recombinant tPA produced under elevated $pCO_2$, Biotechnol. Prog. 13: 311–317 (1997)

Kovar J et al., Iron compounds at high concentrations enable mouse hybridoma and myeloma cells to grow in protein-free medium, Eur. Congr. Biotechnol (1987)

Leibovitz A, The growth and maintenance of tissue-cell cultures in free gas exchange with the atmosphere, Am. J. Hyg. 78: 173–180 (1963)

Medi-cult, Pat. No. EP-; EP-274445; 13.07.88 (1988)

Merck-USA, Eur. Pat. No. 358508 (1990)

Michaels J D et al., Sparging and agitation-induced injury of cultured animal cells: Do cell-to-bubble interactions in the bulk liquid injure cells?, Biotechnol Bioeng. 51: 399–409 (1996)

Nagira K et al., Development of a protein-free medium with iron salts replacing transferrin for a human-human hybridoma, Biosci. Biotechnol. Biochem. 59: 743–745 (1995)

Nagira K et al., Effects of organic pH buffers on a cell growth and an antibody production of human-human hybridoma HB4C5 cells in a serum-free culture, Cytotechnol. 17: 117–125 (1995)

Nakanishi S et al., KS-505a, a novel inhibitor of bovine brain Ca2+ and calmodulin-dependent cyclic-nucleotide-phosphodiesterase, J. Antibiot. 45: 341–347 (1992)

Novo-Nordisk, Pat. No. WO09300423 (1993)

Swim H et al., Nonbicarbonate buffers in cell culture media, Science, 122:466 (1955)

Tung A S et al., Mammalian cell culture: replacement of transferrin by synthetic iron chelators, American Chemical Society, 196th Meeting (1988)

Wan N C et al., U.S. Pat. No. 5,691,202 (1997)

White G P et al., The effect of chelating agents on iron mobilization in Chang cell cultures, Blood. 48: 923–929 (1976)

Wolfe R A, Media for cell culture, In: G. Stephanopoulos (eds.) Biotechnology: Bioprocessing, VCH, Weinheim. Vol. 3, pp. 141–156 (1993)

Yabe N et al., Role of iron chelators in growth-promoting effect on mouse hybridoma cells in a chemically defined medium, In Vitro Cel Dev Biol. 23: 815–820 (1987)

Zhang J et al., Development of a defined medium fermentation process for physostigmine production by Streptomyces griseofuscus, Appl. Microbiol. Biotechnol. 44: 568–575 (1996)

What is claimed is:

1. A cell culture medium, comprising:
   an organic buffer selected from the group consisting of 3-(N-morpholino)propanesulfonic acid, N,N-bis (2-hydroxyethyl)-2-aminoethanesulfonic acid, N-tris (hydroxymethyl)methyl-2-aminoethanesulfonic acid, and tris(hydroxymethyl)aminoethane, wherein the buffer concentration is greater than 2 millimolar,
   a metal complexing agent selected from the group consisting of histidine, iminodiacetic acid, citrate, phosphoserine, aurintricarboxylate and, lysine hydroxamate, wherein the complexing agent concentration is greater than 5 millimolar, and
   less than approximately 1 gram/L of added sodium bicarbonate.

2. The cell culture medium of claim 1, wherein the organic buffer is between approximately 10 and 40 millimolar 3-(N-morpholino)propanesulfonic acid, and the metal complexing agent is between 5 and approximately 30 millimolar histidine.

3. The cell culture medium of claim 1, wherein the organic buffer is between approximately 10 and 40 millimolar N,N-bis (2-hydroxyethyl)-2-aminoethanesulfonic acid, and the metal complexing agent is between 5 and approximately 30 millimolar histidine.

4. The cell culture medium of claim 1, wherein the organic buffer is between approximately 10 and 40 millimolar N-tris(hydroxymethyl)methyl-2-aminoethanesulfonic acid, and the metal complexing agent is between 5 and approximately 30 millimolar histidine.

5. The cell culture medium of claim 1, wherein the organic buffer is between approximately 10 and 40 millimolar tris(hydroxymethyl)aminoethane, and the metal complexing agent is between 5 and approximately 30 millimolar histidine.

6. The cell culture medium of claim 1, where in the medium is essentially free of sodium bicarbonate.

7. A method of culturing mammalian cells under low dissolved $CO_2$ concentration, the method comprising culturing mammalian cells in a medium according to claim 1, said medium being supplied to the cells via a supply line, while adjusting the pH of the medium by adding a source of hydroxide ion to the medium in the supply line.

8. A high-density mammalian cell culture system comprising actively growing mammalian cells and a culture medium according to claim 1.

9. The cell culture medium of claim 1, wherein the organic buffer is approximately 20 millimolar 3-(N-morpholino)propanesulfonic acid, and the metal complexing agent is approximately 10 millimolar histidine.

10. The cell culture medium of claim 3, wherein the organic buffer is approximately 20 millimolar N,N-bis (2-hydroxyethyl)-2-aminoethanesulfonic acid, and the metal complexing agent is approximately 10 millimolar histidine.

11. The cell culture medium of claim 4, wherein the organic buffer is approximately 20 millimolar N-tris (hydroxymethyl)methyl-2-aminoethanesulfonic acid, and the metal complexing agent is approximately 10 millimolar histidine.

12. The cell culture medium of claim 5, wherein the organic buffer is approximately 20 millimolar tris (hydroxymethyl)aminoethane, and the metal complexing agent is approximately 10 millimolar histidine.

13. The method of claim 7, wherein the mammalian cells comprise BHK (baby hamster kidney) cells, CHO (Chinese hamster ovary) cells, HEK (human embryonic kidney) cells, HeLa human cervical carcinoma) cell, L cells (mouse connective tissue), MDCK (Madin Darby canine kidney) cells, Vero (African green monkey kidney) cells, or hybridoma cells.

14. The high-density mammalian cell culture system of claim 8, wherein the actively growing mammalian cells have been engineered to produce recombinant Factor VIII.

* * * * *